US012575778B2

(12) United States Patent
Hatano et al.

(10) Patent No.: US 12,575,778 B2
(45) Date of Patent: Mar. 17, 2026

(54) ELECTROCARDIOGRAM ANALYZING APPARATUS, ELECTROCARDIOGRAM ANALYSIS METHOD, AND NON-TRANSITORY COMPUTER-READABLE STORAGE MEDIUM

(71) Applicant: Cardio Intelligence Inc., Tokyo (JP)

(72) Inventors: Kaoru Hatano, Tokyo (JP); Mineki Takechi, Tokyo (JP); Tomohiro Takata, Tokyo (JP); Hirohisa Taniguchi, Tokyo (JP); Yuichi Tamura, Tokyo (JP)

(73) Assignee: CARDIO INTELLIGENCE INC., Tokyo (JP)

( * ) Notice: Subject to any disclaimer, the term of this patent is extended or adjusted under 35 U.S.C. 154(b) by 0 days.

(21) Appl. No.: 18/395,761

(22) Filed: Dec. 26, 2023

(65) Prior Publication Data

US 2024/0122521 A1     Apr. 18, 2024

Related U.S. Application Data

(63) Continuation of application No. PCT/JP2023/009775, filed on Mar. 14, 2023.

(30) Foreign Application Priority Data

Apr. 11, 2022     (JP) ................................ 2022-065008

(51) Int. Cl.
*A61B 5/35*          (2021.01)
*A61B 5/00*          (2006.01)
               (Continued)

(52) U.S. Cl.
CPC ................ *A61B 5/35* (2021.01); *A61B 5/339* (2021.01); *A61B 5/364* (2021.01); *A61B 5/7267* (2013.01)

(58) Field of Classification Search
CPC .......... A61B 5/35; A61B 5/339; A61B 5/364; A61B 5/7267
See application file for complete search history.

(56) References Cited

U.S. PATENT DOCUMENTS

2006/0247707 A1    11/2006  Meyer et al.
2010/0049069 A1     2/2010  Tarassenko et al.
                  (Continued)

FOREIGN PATENT DOCUMENTS

CN          105307566 A  *  2/2016  ............. A61B 5/044
CN          112842351 A     5/2021
                  (Continued)

*Primary Examiner* — Unsu Jung
*Assistant Examiner* — Laura Hodge
(74) *Attorney, Agent, or Firm* — HAUPTMAN HAM, LLP

(57) ABSTRACT

An electrocardiogram analyzing apparatus has: an acquiring section acquiring a plurality of electrocardiogram waveforms; a classifying section classifying the plurality of electrocardiogram waveforms into a plurality of groups on a basis of shape similarity; an accepting section accepting a reference position of a predetermined type of wave designated on a representative waveform corresponding to at least one electrocardiogram waveform belonging to a selection group selected from the plurality of groups; and an analyzing section identifying correspondence between a plurality of positions, along a time axis, on the representative waveform of a group to which a subject-of-analysis electrocardiogram waveform belongs, and a plurality of positions on the subject-of-analysis electrocardiogram waveform along a time axis, and decides, as a position of the predetermined type of wave included in the subject-of-analysis electrocardiogram waveform, a position on the subject-of-analysis electrocardiogram waveform corresponding to the reference position on the representative waveform represented by the correspondence.

14 Claims, 9 Drawing Sheets

(51) Int. Cl.
    *A61B 5/339*       (2021.01)
    *A61B 5/364*       (2021.01)

(56)           References Cited

U.S. PATENT DOCUMENTS

| | | | |
|---|---|---|---|
| 2013/0109988 A1* | 5/2013 | Kim | A61B 5/742 |
| | | | 600/523 |
| 2014/0336522 A1 | 11/2014 | Nakata et al. | |
| 2015/0250400 A1* | 9/2015 | Takizawa | A61B 5/316 |
| | | | 600/509 |
| 2018/0032691 A1* | 2/2018 | Zur | A61B 5/259 |
| 2019/0313980 A1* | 10/2019 | Yoon | A61B 5/0205 |
| 2020/0113459 A1* | 4/2020 | Jäntti | G16H 40/63 |
| 2020/0352440 A1* | 11/2020 | Shmid | G16H 80/00 |
| 2021/0219904 A1* | 7/2021 | Yarnitsky | A61B 5/36 |
| 2022/0130548 A1 | 4/2022 | Tamura et al. | |

FOREIGN PATENT DOCUMENTS

| | | | | |
|---|---|---|---|---|
| CN | 113786202 A | * | 12/2021 | A61B 5/349 |
| JP | 2007195693 A | | 8/2007 | |
| JP | 2008539038 A | | 11/2008 | |
| JP | 2010057615 A | | 3/2010 | |
| JP | 2010510851 A | | 4/2010 | |
| JP | 2011143118 A | | 7/2011 | |
| JP | 2017192607 A | | 10/2017 | |
| KR | 2017006496 | * | 12/2017 | |
| WO | 2013114596 A1 | | 8/2013 | |
| WO | 2021019984 A1 | | 2/2021 | |

* cited by examiner

ELECTROCARDIOGRAM
DATA

ELECTROCARDIOGRAM
WAVEFORM

ELECTROCARDIOGRAM ANALYZING APPARATUS, ELECTROCARDIOGRAM ANALYSIS METHOD, AND NON-TRANSITORY COMPUTER-READABLE STORAGE MEDIUM

CROSS-REFERENCE TO RELATED APPLICATIONS

The present application is a continuation application of International Application number PCT/JP2023/009775, filed on Mar. 14, 2023, which claims priority under 35 U.S.C § 119(a) to Japanese Patent Application No. 2022-065008, filed on Apr. 11, 2022. The contents of these applications are incorporated herein by reference in their entirety.

BACKGROUND OF THE INVENTION

The present disclosure relates to an electrocardiogram analyzing apparatus, an electrocardiogram analysis method, and a non-transitory computer-readable storage medium for analyzing electrocardiograms.

There are conventionally known Holter electrocardiographs that can generate an electrocardiogram over a long time by being worn on the body of a subject of analysis such as a patient (e.g. see Japanese Patent Application Publication No. 2007-195693).

In order to determine whether or not an anomaly has occurred to an electrocardiogram waveform, characteristic waves such as Q waves, R waves, S waves, or T waves have customarily been observed. For example, in a case where a medicine that may extend the interval between a Q wave and a T wave (hereinafter, a QT interval) as a side effect is administered to a patient, it is required to measure QT intervals of the patient. However, for example, it is known that T waves include variations of forms such as normal T waves, flat T waves, negative T waves, biphasic T waves, or waves which are fusions of T waves and U waves, and it is difficult in some cases for a computer to highly precisely sense the positions of various variations of waves from an electrocardiogram waveform.

BRIEF SUMMARY OF THE INVENTION

Therefore, the present disclosure has been made in view of these matters, and an object thereof is to improve the precision of sensing of the positions of predetermined types of wave on an electrocardiogram waveform.

An electrocardiogram analyzing apparatus according to a first aspect of the present disclosure has: an acquiring section that acquires a plurality of electrocardiogram waveforms generated by dividing electrocardiogram data into heartbeat-by-heartbeat pieces of data; a classifying section that classifies the plurality of electrocardiogram waveforms into a plurality of groups on a basis of shape similarity; an accepting section that accepts a reference position of a predetermined type of wave designated on a representative waveform corresponding to at least one electrocardiogram waveform belonging to a selection group selected from the plurality of groups; and an analyzing section that identifies correspondence between a plurality of positions, along a time axis, on the representative waveform of a group to which a subject-of-analysis electrocardiogram waveform belongs, and a plurality of positions on the subject-of-analysis electrocardiogram waveform along a time axis, and decides, as a position of the predetermined type of wave included in the subject-of-analysis electrocardiogram waveform, a position on the subject-of-analysis electrocardiogram waveform corresponding to the reference position on the representative waveform represented by the correspondence.

An electrocardiogram analysis method according to a second aspect of the present disclosure has steps, executed by a processor, of: acquiring a plurality of electrocardiogram waveforms generated by dividing electrocardiogram data into heartbeat-by-heartbeat pieces of data; classifying the plurality of electrocardiogram waveforms into a plurality of groups on a basis of shape similarity; accepting a reference position of a predetermined type of wave designated on a representative waveform corresponding to at least one electrocardiogram waveform belonging to a selection group selected from the plurality of groups; and identifying correspondence between a plurality of positions, along a time axis, on the representative waveform of a group to which a subject-of-analysis electrocardiogram waveform belongs, and a plurality of positions on the subject-of-analysis electrocardiogram waveform along a time axis, and deciding, as a position of the predetermined type of wave included in the subject-of-analysis electrocardiogram waveform, a position on the subject-of-analysis electrocardiogram waveform corresponding to the reference position on the representative waveform represented by the correspondence.

A program stored on a non-transitory computer-readable storage medium according to a third aspect of the present disclosure causes a computer to function as: an acquiring section that acquires a plurality of electrocardiogram waveforms generated by dividing electrocardiogram data into heartbeat-by-heartbeat pieces of data; a classifying section that classifies the plurality of electrocardiogram waveforms into a plurality of groups on a basis of shape similarity; an accepting section that accepts a reference position of a predetermined type of wave designated on a representative waveform corresponding to at least one electrocardiogram waveform belonging to a selection group selected from the plurality of groups; and an analyzing section that identifies correspondence between a plurality of positions, along a time axis, on the representative waveform of a group to which a subject-of-analysis electrocardiogram waveform belongs, and a plurality of positions on the subject-of-analysis electrocardiogram waveform along a time axis, and decides, as a position of the predetermined type of wave included in the subject-of-analysis electrocardiogram waveform, a position on the subject-of-analysis electrocardiogram waveform corresponding to the reference position on the representative waveform represented by the correspondence.

DETAILED DESCRIPTION OF THE INVENTION

Although the present disclosure is explained below by using an embodiment of the disclosure, the following embodiment does not limit the disclosure according to claims, and all combinations of features explained in the embodiment are not necessarily essential for solutions according to the disclosure.

[Overview of Electrocardiogram Analysis System S]

Figure 1:
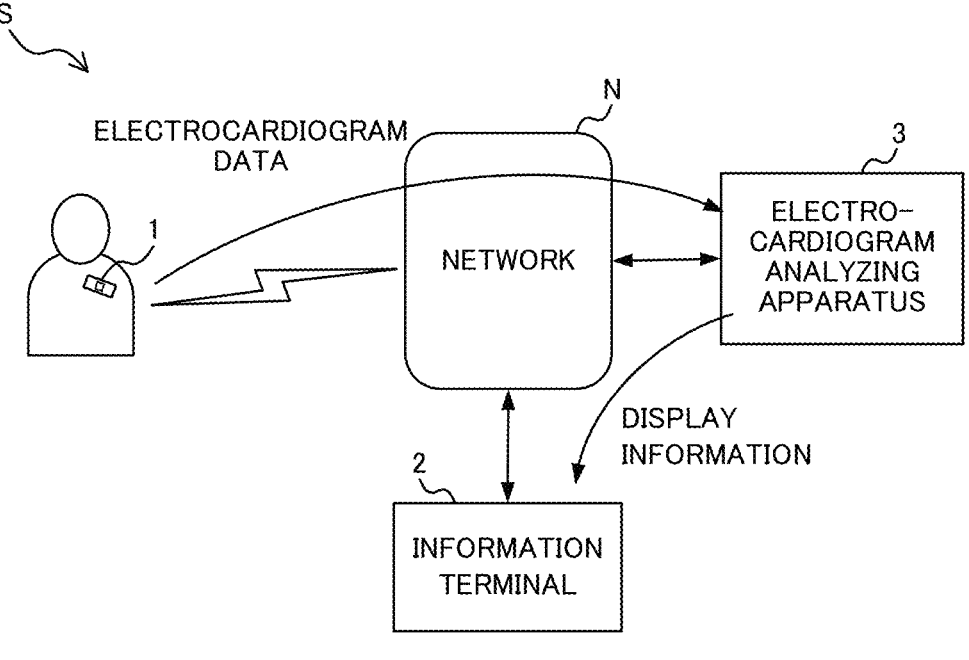
FIG. 1 is a figure for explaining an overview of an electrocardiogram analysis system according to an embodiment.

FIG. 1 is a figure for explaining an overview of an electrocardiogram analysis system S according to the present embodiment. The electrocardiogram analysis system S includes an electrocardiograph 1, an information terminal 2, and an electrocardiogram analyzing apparatus 3. The electrocardiogram analysis system S may include a plurality of electrocardiographs 1 and a plurality of information terminals 2. The electrocardiogram analysis system S may include other equipment such as a server or a terminal.

The electrocardiograph 1 is an apparatus that generates an electrocardiogram of the heart of a subject of analysis. For example, the subject of analysis is a patient undergoing a medical treatment, a subject of a clinical study, or the like. For example, the electrocardiograph 1 is a 12 induction electrocardiograph, a Holter electrocardiograph, an embedded-type electrocardiograph, an event-type electrocardiograph, a patch-type electrocardiograph, or the like that generates an electrocardiogram of the subject of analysis by measuring potential in a state where the subject of analysis has the electrocardiograph 1 on her/his wrist, palm, chest, or the like. In the present embodiment, the electrocardiograph 1 is a patch-type electrocardiograph that can continuously generate an electrocardiogram of the subject of analysis during her/his daily life by being pasted onto the chest of the subject of analysis. In addition, the electrocardiograph 1 may be another apparatus that can generate an electrocardiogram such as a pacemaker, a defibrillator, or an endocardiac electrode.

The electrocardiograph 1 transmits, to the electrocardiogram analyzing apparatus 3, electrocardiogram data representing a generated electrocardiogram via a network N including a wireless communication line. The electrocardiogram data generated by the electrocardiograph 1 may be input to the electrocardiogram analyzing apparatus 3 by using a storage medium, for example, without being transmitted via the network N.

The information terminal 2 is a computer used by an analyst such as a doctor or a health care worker. For example, the information terminal 2 has a display section such as a liquid crystal display that can display information received from the electrocardiogram analyzing apparatus 3, and an operation section such as a keyboard or a mouse to be operated by the analyst.

The electrocardiogram analyzing apparatus 3 is a computer for analyzing electrical activities of the heart. For example, on the basis of the electrocardiogram data received from the electrocardiograph 1, the electrocardiogram analyzing apparatus 3 decides the positions of predetermined types of wave such as a Q wave or a T wave, and outputs information about the positions of the predetermined types of wave such as a QT interval.

An overview of a process executed by the electrocardiogram analysis system S according to the present embodiment is explained below. The electrocardiograph 1 generates an electrocardiogram of a subject of analysis having the electrocardiograph 1 on. The electrocardiograph 1 transmits electrocardiogram data representing the generated electrocardiogram to the electrocardiogram analyzing apparatus 3.

The electrocardiogram analyzing apparatus 3 receives the electrocardiogram data transmitted by the electrocardiograph 1. The electrocardiogram analyzing apparatus 3 acquires a plurality of electrocardiogram waveforms by dividing the received electrocardiogram data (e.g. electrocardiogram data of 24 hours over which measurement was performed for the one subject of analysis) into heartbeat-by-heartbeat pieces of data. For example, by taking out a waveform corresponding to one period from a waveform including a plurality of periods included in the received electrocardiogram data, the electrocardiogram analyzing apparatus 3 generates data representing, as an electrocardiogram waveform of one beat, a waveform of the one period. For example, by executing a clustering process on the acquired plurality of electrocardiogram waveforms, the electrocardiogram analyzing apparatus 3 classifies the plurality of electrocardiogram waveforms into a plurality of groups on the basis of shape similarity.

The electrocardiogram analyzing apparatus 3 causes the information terminal 2 to display a representative waveform which is at least one electrocardiogram waveform belonging to each group, and accepts designation of the positions (reference positions) of predetermined types of wave (a Q wave, a T wave, etc.) on the representative waveform from an analyst.

The electrocardiogram analyzing apparatus 3 identifies the correspondence between a plurality of positions, along the time axis, on a representative waveform of a group to which a subject-of-analysis electrocardiogram waveform belongs, and a plurality of positions on the subject-of-analysis electrocardiogram waveform along the time axis. For example, the electrocardiogram analyzing apparatus 3 associates points on the representative waveform and points on the subject-of-analysis electrocardiogram waveform with each other by a DTW method (Dynamic Time Warping; dynamic time warping).

The electrocardiogram analyzing apparatus 3 decides, as the positions of predetermined types of wave included in the subject-of-analysis electrocardiogram waveform, positions on the subject-of-analysis electrocardiogram waveform corresponding to the reference positions on the representative waveform represented by the identified correspondence.

The electrocardiogram analyzing apparatus 3 transmits, to the information terminal 2, display information for displaying information (e.g. a QT interval) about the decided positions of the predetermined types of wave. On the basis of the display information received from the electrocardiogram analyzing apparatus 3, the information terminal 2 displays the information about the positions of the predetermined types of wave on the display section.

For example, it is known that T waves include various variations of forms such as normal T waves, flat T waves, or negative T waves. The electrocardiogram analysis system S decides the positions of predetermined types of wave in the subject-of-analysis electrocardiogram waveform by classifying heartbeat-by-heartbeat electrocardiogram waveforms into a plurality of groups on the basis of shape similarity, and accepting, from an analyst, designation of the positions of predetermined types of wave on a representative waveform of each group. Thereby, the electrocardiogram analysis system S can decide the positions of the predetermined type of waves taking into consideration variations of forms of waves, and can improve the precision of sensing of the positions of the predetermined types of wave in the electrocardiogram waveform.

[Configuration of Electrocardiogram Analysis System S]

Figure 2:
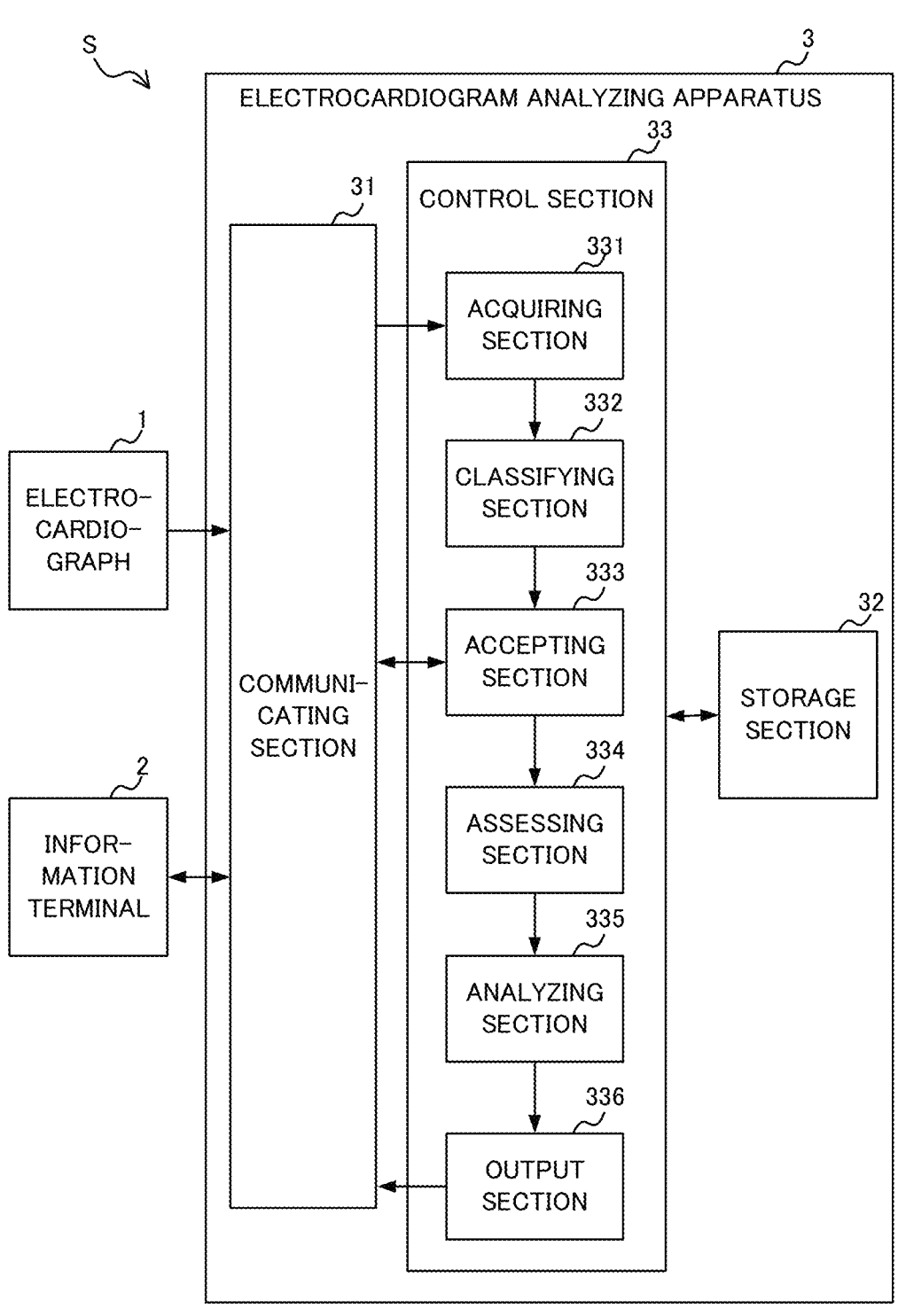
FIG. 2 is a block diagram of the electrocardiogram analysis system according to the embodiment.

FIG. 2 is a block diagram of the electrocardiogram analysis system S according to the present embodiment. In FIG. 2, arrows represent main data flows, and there may be data flows other than those depicted in FIG. 2. In FIG. 2, each block represents not the configuration of a piece of hardware (apparatus), but the configuration of a function. Accordingly, blocks depicted in FIG. 2 may be implemented in a single apparatus, or may be implemented separately in a plurality of apparatuses. Data exchange between the blocks may be performed via any means such as a data bus, a network, or a portable storage medium.

The electrocardiogram analyzing apparatus 3 has a communicating section 31, a storage section 32, and a control section 33. The electrocardiogram analyzing apparatus 3 may be configured by connecting two or more physically separate apparatuses by a wire or wirelessly. In addition, the electrocardiogram analyzing apparatus 3 may be configured by cloud computing using a set of computer resources.

The communicating section 31 has a communication controller for data transmission and reception between the electrocardiograph 1 and the information terminal 2 via the network N. The communicating section 31 notifies the control section 33 of data received from the electrocardiograph 1 and the information terminal 2 via the network N. In addition, the communicating section 31 transmits data output from the control section 33 to the information terminal 2 via the network N.

The storage section 32 is a storage medium including a ROM (Read Only Memory), a RAM (Random Access Memory), a hard disk drive, or the like. The storage section 32 has stored thereon in advance programs to be executed by the control section 33. The storage section 32 may be provided outside the electrocardiogram analyzing apparatus 3, and, in that case, may perform data exchange with the control section 33 via a network.

The control section 33 has an acquiring section 331, a classifying section 332, an accepting section 333, an assessing section 334, an analyzing section 335, and an output section 336. For example, the control section 33 is a processor such as a CPU (Central Processing Unit), and functions as the acquiring section 331, the classifying section 332, the accepting section 333, the assessing section 334, the analyzing section 335, and the output section 336 by executing programs stored on the storage section 32. At least some of the functions of the control section 33 may be executed by electrical circuits. In addition, at least some of the functions of the control section 33 may be realized by the control section 33 executing programs executed through a network.

Hereinbelow, a display control method executed by the electrocardiogram analysis system S according to the present embodiment is explained in detail. A subject of analysis wears the electrocardiograph 1. The electrocardiograph 1 generates an electrocardiogram of the subject of analysis having the electrocardiograph 1 on. The electrocardiograph 1 transmits electrocardiogram data representing the generated electrocardiogram to the electrocardiogram analyzing apparatus 3. The electrocardiograph 1 serially transmits the electrocardiogram data to the electrocardiogram analyzing apparatus 3, or collectively transmits the electrocardiogram data of a predetermined period (e.g. 24 hours) to the electrocardiogram analyzing apparatus 3.

In the electrocardiogram analyzing apparatus 3, the acquiring section 331 receives the electrocardiogram data transmitted by the electrocardiograph 1 via the communicating section 31. The acquiring section 331 acquires a plurality of electrocardiogram waveforms generated by dividing the received electrocardiogram data (i.e. electrocardiogram data of the one patient) into heartbeat-by-heartbeat pieces of data.

Figure 3:
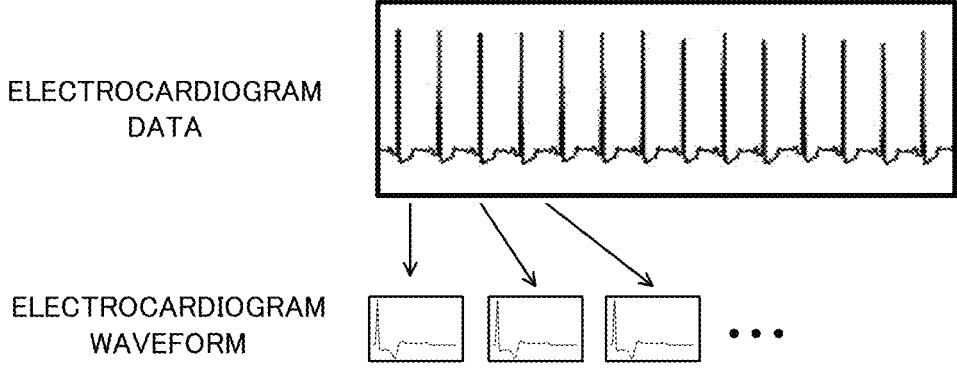
FIG. 3 is a schematic diagram for explaining a method by which an acquiring section divides electrocardiogram data into heartbeat-by-heartbeat pieces of data.

FIG. 3 is a schematic diagram for explaining a method by which the acquiring section 331 divides electrocardiogram data into heartbeat-by-heartbeat pieces of data. For example, the acquiring section 331 senses the positions of peaks of R waves in the electrocardiogram data, and acquires, as an electrocardiogram waveform of one beat, a waveform of a segment that starts a predetermined length of time before the peak of an R wave, and ends a predetermined length of time after the peak of the next R wave. The method to be used by the acquiring section 331 is not limited to the specific method depicted here, but the acquiring section 331 may divide the electrocardiogram data into heartbeat-by-heartbeat pieces of data by another method.

The acquiring section 331 may execute a noise removal process on the electrocardiogram data. For example, the acquiring section 331 inputs each of a plurality of segmented electrocardiograms generated by segmenting the electrocardiogram data to a machine learning model that is generated by prior machine learning using exclusion-subject electrocardiograms (electrocardiograms including noise or extrasystoles), and subject-of-analysis electrocardiograms, and assesses whether or not an input electrocardiogram is an subject of exclusion. Then, the acquiring section 331 acquires a plurality of electrocardiogram waveforms by dividing segmented electrocardiograms assessed as being not subjects of exclusion by the machine learning model into heartbeat-by-heartbeat electrocardiograms.

In addition, for example, the acquiring section 331 may exclude an electrocardiogram waveform with a heart rate per unit time which is higher than or lower than a predetermined threshold from a plurality of electrocardiogram waveforms acquired from the electrocardiogram data.

Figure 4:
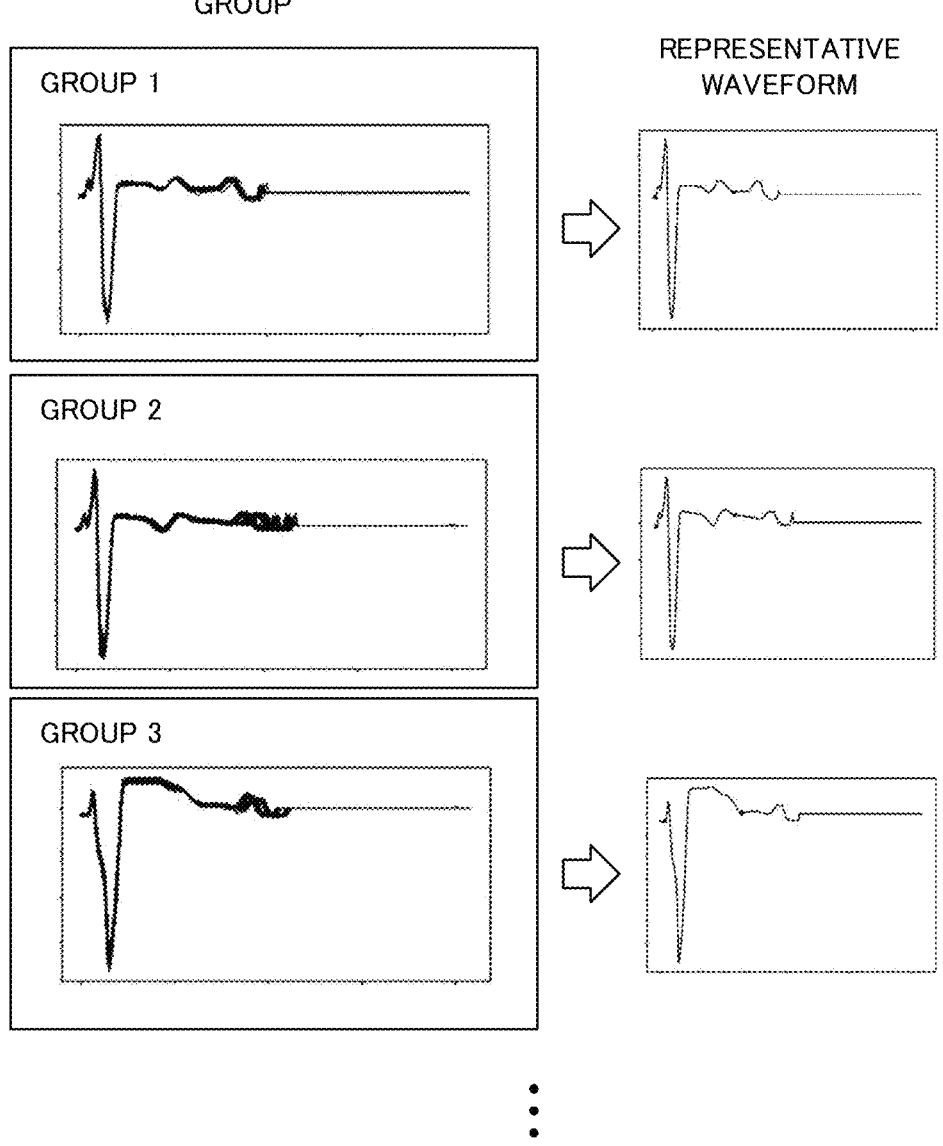
FIG. 4 is a schematic diagram for explaining a method by which a classifying section classifies a plurality of electrocardiogram waveforms into a plurality of groups.

The classifying section 332 classifies the plurality of electrocardiogram waveforms acquired by the acquiring section 331 into a plurality of groups on the basis of shape similarity. FIG. 4 is a schematic diagram for explaining a method by which the classifying section 332 classifies a plurality of electrocardiogram waveforms into a plurality of groups. The left side of FIG. 4 depicts a plurality of superimposed electrocardiogram waveforms belonging to each group, and the right side of FIG. 4 depicts a representative waveform of each group.

As depicted in FIG. 4, electrocardiogram waveforms include various variations of forms. In the example in FIG. 4, electrocardiogram waveforms of the same patient include second T waves of biphasic T waves that end with flat waveforms, second T waves of biphasic T waves that end with gently and continuously descending signal waveforms, and T waves with shapes that changed significantly during measurement. Conventionally, if one attempts to automatically sense the positions of particular types of wave on electrocardiogram waveforms without taking into consideration such variations of forms, for example, points after descending waveforms of T waves are erroneously sensed as the terminating ends of the T waves, in some cases.

For example, the classifying section 332 executes a known clustering process on the plurality of electrocardiogram waveforms acquired by the acquiring section 331. For example, the clustering process is a process using the K-Shape method to classify a plurality of electrocardiogram waveforms into a plurality of clusters such that the distances between the shapes of electrocardiogram waveforms in each cluster are short. The classifying section 332 decides the plurality of clusters generated by the clustering process as a plurality of groups generated on the basis of shape similarity.

The method used by the classifying section 332 is not limited to the K-Shape method depicted here, which is a shape-based cluster approach, but the classifying section 332 may classify a plurality of electrocardiogram waveforms into a plurality of groups by another method. For example, as long as the classifying section 332 can associate particular positions (the end positions of T waves, etc.) of a plurality of electrocardiogram waveforms with each other, the classifying section 332 does not necessarily use a clustering process based on shape similarity, but may use another classification approach. For example, as another classification approach, the classifying section 332 can use the K-means method, the DB SCAN method, hierarchical clustering, or the like. In addition, the classifying section 332 may classify a plurality of electrocardiogram waveforms into a plurality of groups by a supervised learning or semi-supervised learning approach.

In the example in FIG. 4, the plurality of electrocardiogram waveforms are classified into: a group including electrocardiogram waveforms whose second T waves of biphasic T waves end with flat waveforms; a group including electrocardiogram waveforms whose second T waves of biphasic T waves end with gently and continuously descending waveforms; and a group including electrocardiogram waveforms whose T waves have shapes that changed significantly during measurement. The plurality of electrocardiogram waveforms are not necessarily classified into three groups, but may be classified into a different number of groups.

The classifying section 332 extracts, from each of the decided plurality of groups, a representative waveform corresponding to at least one electrocardiogram waveform belonging to the group. For example, the classifying section 332 calculates a centroid waveform which is the center of mass of a plurality of electrocardiogram waveforms belonging to one group. The classifying section 332 extracts, as the representative waveform, an electrocardiogram waveform most similar to the centroid waveform (e.g. an electrocardiogram waveform whose Euclidean distance to the centroid waveform is the shortest) from the plurality of electrocardiogram waveforms belonging to the group. In addition, the classifying section 332 may extract the calculated centroid waveform as the representative waveform. In addition, the classifying section 332 may extract, as a plurality of representative waveforms, a plurality of electrocardiogram waveforms belonging to one group.

The classifying section 332 may execute a clustering process multiple times on the plurality of electrocardiogram waveforms acquired by the acquiring section 331, and extract representative waveforms from a plurality of groups generated at each time. In this case, the classifying section 332 may use, as a representative waveform, a statistic (e.g. the average) of a plurality of representative waveforms extracted multiple times. Thereby, the electrocardiogram analyzing apparatus 3 can reduce the influence of localized solutions in the clustering process.

The accepting section 333 accepts designation of reference positions of predetermined types of wave on a representative waveform extracted from each of a plurality of groups. Whereas the predetermined types of wave are Q waves and T waves in the present embodiment, only either of Q waves and T waves or other types of wave such as R waves or S waves may be used.

Figure 5:
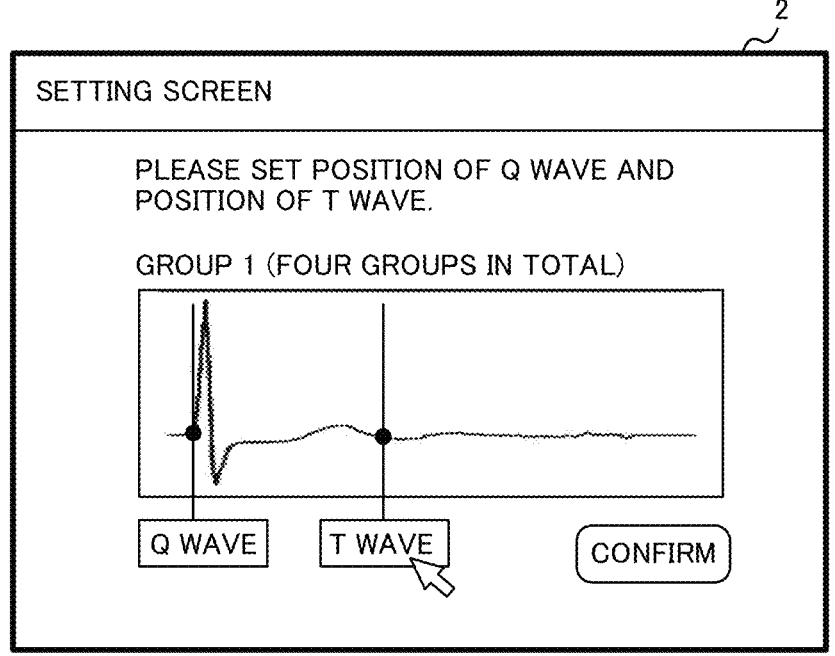
FIG. 5 is a schematic diagram for explaining a method by which an accepting section accepts designation of reference positions on a representative waveform.

FIG. 5 is a schematic diagram for explaining a method by which the accepting section 333 accepts designation of reference positions on a representative waveform. For example, the accepting section 333 transmits, to the information terminal 2 via the communicating section 31, information representing a representative waveform of a selection group which is any one group selected from the plurality of groups.

On the basis of the information received from the electrocardiogram analyzing apparatus 3, the information terminal 2 displays the representative waveform on the display section. Through the operation section, The information terminal 2 accepts, from an analyst, operation to designate the positions of predetermined types of wave (here, a Q wave and a T wave). The information terminal 2 transmits, to the electrocardiogram analyzing apparatus 3, information representing the positions designated by the analyst.

In the electrocardiogram analyzing apparatus 3, the accepting section 333 accepts, as reference positions of predetermined types of wave, the positions represented by the information received from the information terminal 2 via the communicating section 31. In a case where designation of reference positions of all of the plurality of groups has not been accepted, the accepting section 333 transmits, to the information terminal 2 via the communicating section 31, information representing a representative waveform of another selection group in the plurality of groups, and accepts designation of reference positions. In a case where designation of reference positions all of the plurality of groups has been accepted, the accepting section 333 ends accepting designation of reference positions.

Instead of accepting designation of reference positions by an analyst on the information terminal 2, the accepting section 333 may accept, as reference positions, the positions of predetermined types of wave identified on the representative waveforms by the electrocardiogram analyzing apparatus 3 or a second computer. In this case, for example, the electrocardiogram analyzing apparatus 3 or the second computer identifies the positions of the predetermined types of wave on the representative waveforms on the basis of statistical data about the positions of predetermined types of wave designated in the past by one or more analysts on waveforms similar to the representative waveforms. In addition, the accepting section 333 may calculate tentative reference positions by using a predetermined algorithm or the like for each representative waveform, causes the information terminal 2 to display the calculated tentative reference positions and the representative waveform in association with each other, and accept designation of reference positions from an analyst on the information terminal 2 in a case where the analyst determines that it is required to correct the tentative reference positions. Thereby, the electrocardiogram analyzing apparatus 3 can reduce the work of designation of reference positions by the analyst.

The accepting section 333 may accept designation of positions on one representative waveform on the information terminal 2 multiple times, and accept, as a reference position, a statistic (e.g. the average) of a plurality of designated positions. In addition, the accepting section 333 may accept designation of positions on each of a plurality of representative waveforms extracted from one group on the information terminal 2, and accept, as a reference position, a statistic (e.g. the average) of a plurality of designated positions. Thereby, the electrocardiogram analyzing apparatus 3 can reduce the influence of variations of the positions of predetermined types of wave designated by an analyst.

Before the analyzing section 335 performs a process of deciding the positions of predetermined types of wave, the assessing section 334 assesses whether or not each of a plurality of electrocardiogram waveforms is anomalous (outlier). For example, the assessing section 334 calculates the similarity between each of a plurality of electrocardiogram waveforms belonging to one group and a waveform which is a statistic (e.g. the centroid waveform) of the plurality of electrocardiogram waveforms belonging to the group. For example, the similarity is the Euclidean distance. In a case where the similarity calculated for one electrocardiogram waveform is equal to or higher than a predetermined threshold, the assessing section 334 assesses that the electrocardiogram waveform is not anomalous, and in a case where the similarity is lower than the threshold, the assessing section 334 assesses that the electrocardiogram waveform is anomalous.

The analyzing section 335 performs the following process treating, as a subject-of-analysis electrocardiogram waveform, each of a plurality of electrocardiogram waveforms belonging to one group. The analyzing section 335 identifies the correspondence between a plurality of positions, along the time axis, on a representative waveform of the group to which a subject-of-analysis electrocardiogram waveform belongs, and a plurality of positions on the subject-of-analysis electrocardiogram waveform along the time axis.

Figure 6:
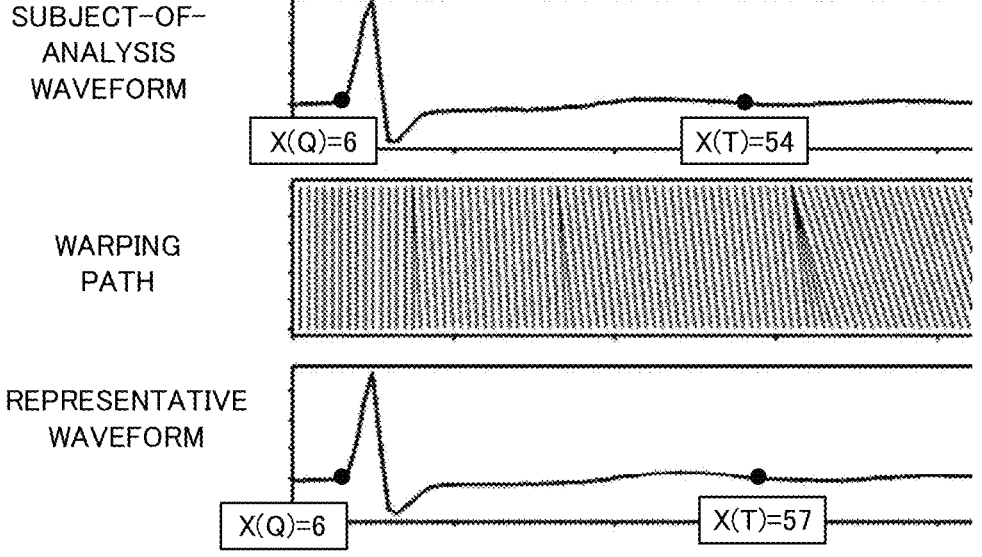
FIG. 6 is a schematic diagram for explaining a method by which an analyzing section identifies the correspondence between a representative waveform and a subject-of-analysis electrocardiogram waveform.

FIG. 6 is a schematic diagram for explaining a method by which the analyzing section 335 identifies the correspondence between a representative waveform and a subject-of-analysis electrocardiogram waveform. For example, by the DTW method, the analyzing section 335 calculates the distance between each of a plurality of points (coordinates) on the representative waveform arranged at predetermined time intervals, and each of a plurality of points on the subject-of-analysis electrocardiogram waveform arranged at predetermined time intervals, by a round-robin approach. The analyzing section 335 sequentially associates the plurality of points on the representative waveform and the plurality of points on the subject-of-analysis electrocardiogram waveform with each other such that the total value of the calculated distances is minimized. FIG. 6 depicts line segments (also referred to as warping paths) connecting points on the subject-of-analysis electrocardiogram waveform and points on the representative waveform that are associated with the points.

The analyzing section 335 identifies, as correspondence, combinations of each of the plurality of points on the subject-of-analysis electrocardiogram waveform and a point on the representative waveform associated with the point. The method used by the analyzing section 335 is not limited to the specific method depicted here, but the analyzing section 335 may identify the correspondence between the representative waveform and the subject-of-analysis by another method.

The analyzing section 335 decides, as the positions of predetermined types of wave included in the subject-of-analysis electrocardiogram waveform, positions on the subject-of-analysis electrocardiogram waveform corresponding to reference positions on the representative waveform represented by the identified correspondence. That is, by identifying to which points on the subject-of-analysis electrocardiogram waveform reference positions of predetermined types of wave designated on the representative waveform correspond, the analyzing section 335 decides the positions of the predetermined types of wave included in the subject-of-analysis electrocardiogram waveform.

In the example in FIG. 6, a reference position of a Q wave is at the sixth point on the representative waveform, and the sixth point on the representative waveform corresponds to the sixth point on the subject-of-analysis electrocardiogram waveform. Accordingly, the analyzing section 335 decides that the position of the Q wave included in the subject-of-analysis electrocardiogram waveform is at the sixth point on the subject-of-analysis electrocardiogram waveform. In addition, a reference position of a T wave is at the fifty-seventh point on the representative waveform, and the fifty-seventh point on the representative waveform corresponds to the fifty-fourth point on the subject-of-analysis electrocardiogram waveform. Accordingly, the analyzing section 335 decides that the position of the T wave included in the subject-of-analysis electrocardiogram waveform is at the fifty-fourth point on the subject-of-analysis electrocardiogram waveform.

Since various types of wave such as normal T waves, flat T waves, or negative T waves have forms that are different from each other, it has conventionally been difficult for a computer to highly precisely sense the positions of the various types of wave from an electrocardiogram waveform, in some cases. To cope with this, the electrocardiogram analyzing apparatus 3 can improve the precision of sensing of the positions of predetermined types of wave included in a subject-of-analysis electrocardiogram waveform taking into consideration variations of forms of waves by deciding the positions of the predetermined types of wave by using positions designated on representative waveforms of groups generated on the basis of shape similarity.

Under a condition that a subject-of-analysis electrocardiogram waveform is assessed as being not anomalous by the assessing section 334, the analyzing section 335 may decide the positions of predetermined types of wave. In this case, the analyzing section 335 decides the positions of predetermined types of wave on an electrocardiogram waveform assessed as being not anomalous by the assessing section 334 in a plurality of electrocardiogram waveforms, and does not decide the positions of predetermined types of wave on an electrocardiogram waveform assessed as being anomalous by the assessing section 334. Thereby, for example, the electrocardiogram analyzing apparatus 3 can exclude, as an outlier, an electrocardiogram waveform which is significantly different from a statistic (the centroid waveform, etc.) of a plurality of electrocardiogram waveforms belonging to a group, and reduce the occurrence of an alert such as an extension of a QT interval on the basis of the outlier.

The analyzing section 335 generates information about the decided positions of predetermined types of wave. For example, the analyzing section 335 generates information about the positions of predetermined types of wave including a QT interval (hereinafter, a QT) which is the interval between the position of a Q wave and the position of a T wave in one electrocardiogram waveform, and/or a calibrated interval calculated by calibrating QT by using a heart rate identified from the subject-of-analysis electrocardiogram waveform.

For example, the analyzing section 335 calculates the calibrated interval (QTc) by using the following Formula (1) proposed by Bazett. QTc calculated in accordance with Formula (1) is also referred to as QTcB.

[Formula 1]

$$QTc = QT/\sqrt{RR} \qquad (1)$$

RR (RR interval) is the interval between the positions of R waves in two continuous electrocardiogram waveforms, and is the reciprocal of the heart rate. In addition, the analyzing section 335 may calculate QTc by using another known formula such as the Fridericia calibration formula, the Hodges calibration formula, or the Framingham calibration formula.

In addition, the analyzing section 335 may calculate, as QT or QTc of a subject of analysis, a statistic (e.g. the average) of a plurality of QT or QTc calculated from a plurality of electrocardiogram waveforms.

In addition, under a condition that a statistic of QT or QTc of a plurality of electrocardiogram waveforms belonging to one group is equal to or greater than a predetermined threshold, the analyzing section 335 may select a representative electrocardiogram waveform of the group. For example, the analyzing section 335 may select, as a representative electrocardiogram waveform of one group, a representative waveform used for calculation of the position of a wave in the group. For example, the analyzing section 335 may calculate the similarity between each electrocardiogram waveform belonging to one group and a waveform which is a statistic (e.g. the centroid waveform) of a plurality of electrocardiogram waveforms belonging to the group, and select, as representative electrocardiogram waveforms of the group, one or more electrocardiogram waveforms in descending order of the calculated similarity. In addition, the analyzing section 335 may select, as representative electrocardiogram waveforms of one group, one or more electrocardiogram waveforms in descending order of the differences between QT or QTc and a statistic of QT or QTc of a plurality of electrocardiogram waveforms belonging to the group.

For an analyst, it takes significant work to check a plurality of electrocardiogram waveforms belonging to each of a plurality of groups, and a plurality of QT or QTc. In contrast to this, the analyzing section 335 generates information about the positions of predetermined types of wave including an electrocardiogram waveform selected on the basis of a statistic of QT or QTc of a plurality of electrocardiogram waveforms belonging to one group. Thereby, the electrocardiogram analyzing apparatus 3 can present, to an analyst, a representative electrocardiogram waveform belonging to one group in a case where QT or QTc of the group is large (in a case where there is a possibility that there is an extension of QT), and make it easier for the analyst to perform analysis.

The analyzing section 335 may calculate the difference (hereinafter, ΔQT or ΔQTc) between QT or QTc calculated before the administration of a medicine to one subject of analysis, and QT or QTc calculated after the administration of the medicine. In this case, the storage section 32 stores QT or QTc calculated before the administration of a predetermined medicine to a subject of analysis, and QT or QTc calculated after the administration of the predetermined medicine to the subject of analysis in association with each other, and calculates ΔQT or ΔQTc when a predetermined condition is satisfied (e.g. predetermined operation by an analyst was performed on the information terminal 2).

For example, the analyzing section 335 may calculate, as ΔQT or ΔQTc, the difference between the median of QT or QTc in a predetermined period (e.g. 24 hours) before the administration of a medicine, and the median of QT or QTc in a predetermined period (e.g. 24 hours) after the administration of the medicine.

The analyzing section 335 generates information about the positions of predetermined types of wave including calculated ΔQT or ΔQTc. Thereby, the electrocardiogram analyzing apparatus 3 can visualize changes of QT or QTc before and after the administration of the predetermined medicine, and make it easier for an analyst to perform analysis.

In addition, the analyzing section 335 may predict a timing at which ΔQT or ΔQTc exceeds a predetermined threshold (e.g. 450 ms) when the same dose of a medicine is continuously administered, on the basis of the inclination of temporal changes of ΔQT or ΔQTc after the administration of the medicine. When a medicine is continuously administered to a subject of analysis, ΔQT or ΔQTc exceeds a threshold undesirably, in some cases. To cope with this, the analyzing section 335 generates information about the positions of predetermined types of wave including a predicted timing at which ΔQT or ΔQTc exceeds a threshold. Thereby, the electrocardiogram analyzing apparatus 3 can make it easier for an analyst to adjust the dose or administration timing of a medicine for a subject of analysis such that ΔQT or ΔQTc does not exceed a threshold due to the administration of the medicine.

In addition, the analyzing section 335 may assess whether or not the dose of a medicine for a subject of analysis should be reduced or increased on the basis of the description of medicine data (e.g. the package insert about the administration and dose of a medicine) representing characteristics of each medicine stored on the storage section 32. In a case where calculated ΔQT or ΔQTc exceeds a threshold represented by medicine data, the analyzing section 335 assesses that the dose should be reduced, and otherwise the analyzing section 335 assesses that the dose should be increased. The analyzing section 335 generates information about the positions of predetermined types of wave including an assessment result as to whether or not the dose should be reduced or increased. Thereby, the electrocardiogram analyzing apparatus 3 can present, to an analyst, the possibility of a reduction or an increase of the dose according to the package insert of a medicine, and make it easier for the analyst to adjust the dose of the medicine for a subject of analysis.

In addition, the analyzing section 335 may assess whether or not one heartbeat is anomalous on the basis of calculated QT or QTc. For example, in a case where QT or QTc calculated from an electrocardiogram waveform corresponding to one heartbeat is equal to or greater than a predetermined threshold, the analyzing section 335 assesses that the heartbeat is anomalous, and otherwise the analyzing section 335 assesses that the heartbeat is not anomalous.

In addition, the analyzing section 335 may assess whether or not one heartbeat is anomalous on the basis of the relationship between calculated QT or QTc and RR. For example, the analyzing section 335 may generate a scatter plot by plotting QT or QTc calculated from each of a plurality of electrocardiogram waveforms belonging to one group, and RR of the electrocardiogram waveforms, and calculate a fitting curve representing the relationship between QT or QTc and RR on the generated scatter plot. In a case where the distance between a point on an electrocardiogram waveform corresponding to one heartbeat and the fitting curve is equal to or longer than a predetermined threshold, the analyzing section 335 assesses that the heartbeat is anomalous, and otherwise the analyzing section 335 assesses that the heartbeat is not anomalous.

The analyzing section 335 generates information about the positions of predetermined types of wave including information that is different depending on whether it is assessed that the heartbeat is anomalous and it is assessed that the heartbeat is not anomalous. For example, the analyzing section 335 generates, as information about the positions of predetermined types of wave, information for displaying a message representing that it is assessed that a heartbeat is anomalous, along with an electrocardiogram waveform assessed as representing the anomalous heartbeat. Thereby, the electrocardiogram analyzing apparatus 3 can present, to an analyst, an assessment result as to whether or not heartbeats are anomalous, and make it easier for the analyst to perform analysis.

Furthermore, the accepting section 333 may transmit, to the information terminal 2, information representing an electrocardiogram waveform corresponding to a heartbeat assessed as being anomalous by the analyzing section 335, and accept, on the information terminal 2, operation representing an instruction whether to or not to include, in analysis, the heartbeat assessed as being anomalous. In a case where operation representing an instruction not to include, in analysis, the heartbeat assessed as being anomalous was performed on the information terminal 2, the analyzing section 335 recalculates QT or QTc, and performs the following process without using the electrocardiogram waveform corresponding to the heartbeat assessed as being anomalous. On the other hand, in a case where operation representing an instruction to include, in analysis, the heartbeat assessed as being anomalous was performed on the information terminal 2, the analyzing section 335 performs the following process using QT or QTc calculated already. Thereby, the electrocardiogram analyzing apparatus 3 can switch whether to or not to use, for analysis, the electrocardiogram waveform corresponding to the heartbeat assessed as being anomalous in accordance with an intention of an analyst.

In addition, the analyzing section 335 may assess whether or not a group is anomalous on the basis of variations in calculated QT or QTc. For example, the analyzing section 335 calculates the standard deviation of a plurality of QT or QTc calculated from a plurality of electrocardiogram waveforms belonging to one group. In a case where the calculated standard deviation is equal to or greater than a predetermined threshold (15 ms, 20 ms, etc.), the analyzing section 335 assesses that the group is anomalous, and otherwise the analyzing section 335 assesses that the group is not anomalous. In addition, in a case where the number or rate of electrocardiogram waveforms corresponding to heartbeats assessed as being anomalous on the basis of QT or QTc in a plurality of electrocardiogram waveforms belonging to one group is equal to or greater than a predetermined threshold, the analyzing section 335 may assess that the group is anomalous, and otherwise the analyzing section 335 may assess that the group is not anomalous.

The analyzing section 335 generates information about the positions of predetermined types of wave including information that is different depending on whether it is assessed that the group is anomalous and it is assessed that the group is not anomalous. For example, the analyzing section 335 generates, as information about the positions of predetermined types of wave, information for displaying a message representing that it is assessed that a group is anomalous, along with a representative waveform of the group assessed as being anomalous. If a group itself generated by the classifying section 332 is anomalous, analysis of a plurality of electrocardiogram waveforms belonging to the group is not performed correctly in some cases. To cope with this, the electrocardiogram analyzing apparatus 3 can assess that not an electrocardiogram waveform, but a group itself generated by the classifying section 332 is anomalous in a case where variations in electrocardiogram waveforms belonging to the group are large or in other cases.

Furthermore, the accepting section 333 may accept, on the information terminal 2, operation representing an instruction whether to or not to implement designation of reference positions of a group assessed as being anomalous by the analyzing section 335 again. In a case where the operation representing an instruction to implement designation of reference positions was performed on the information terminal 2 again, the accepting section 333 accepts designation of reference positions on a representative waveform of the group assessed as being anomalous by the analyzing section 335 again. Thereby, the electrocardiogram analyzing apparatus 3 can switch whether to or not to redo designation of reference positions of the group assessed as being anomalous in accordance with an intention of an analyst.

Figure 7:
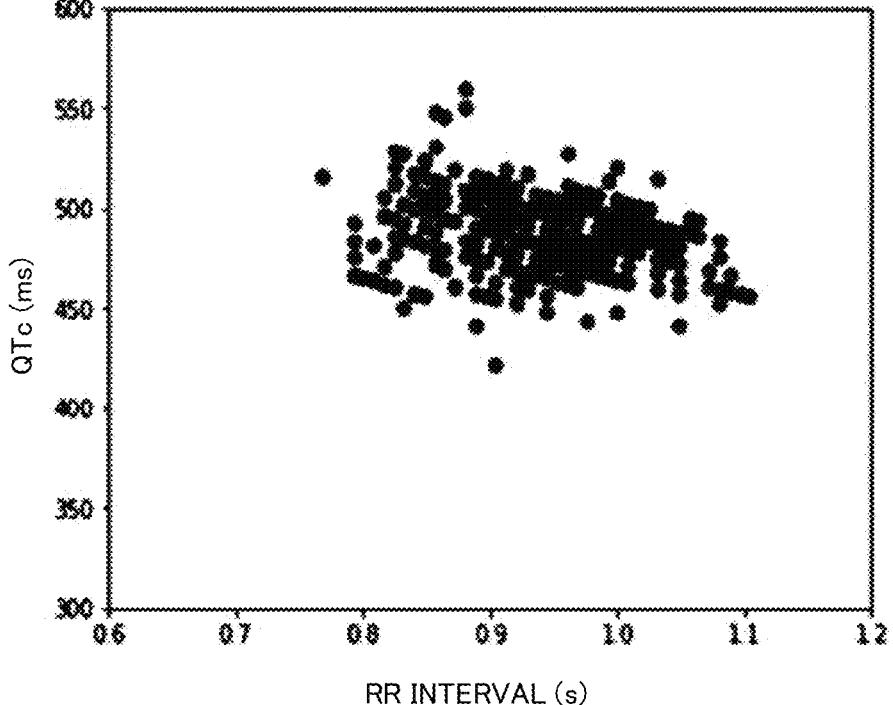
FIG. 7 is a figure depicting an illustrative QTc distribution calculated by the analyzing section for a plurality of electrocardiogram waveforms belonging to one group.

FIG. 7 is a figure depicting an illustrative QTc distribution calculated by the analyzing section 335 for a plurality of electrocardiogram waveforms belonging to one group. In FIG. 7, the horizontal axis represents RR, and the vertical axis represents QTc. The example in FIG. 7 represents a group of flat T waves which are T waves with flat shapes, and it can be known that there is a certain correlation between RR and QTc. Accordingly, the electrocardiogram analyzing apparatus 3 can calculate QTc precisely of even electrocardiogram waveforms with special forms like flat T waves.

The output section 336 outputs information about the positions of predetermined types of wave generated by the analyzing section 335. Under a condition that a predetermined condition is satisfied (e.g. QT, QTc, a statistic of QT, or a statistic of QTc is equal to or greater than a predetermined threshold), the output section 336 may output information about the positions of predetermined types of wave.

For example, the output section 336 transmits, to the information terminal 2 via the communicating section 31, display information for displaying information about the positions of predetermined types of wave. Instead of or in addition to causing the information terminal 2 to display information about the positions of predetermined types of wave, the output section 336 may cause a printing apparatus to print information about the positions of the predetermined types of wave.

Figure 8:
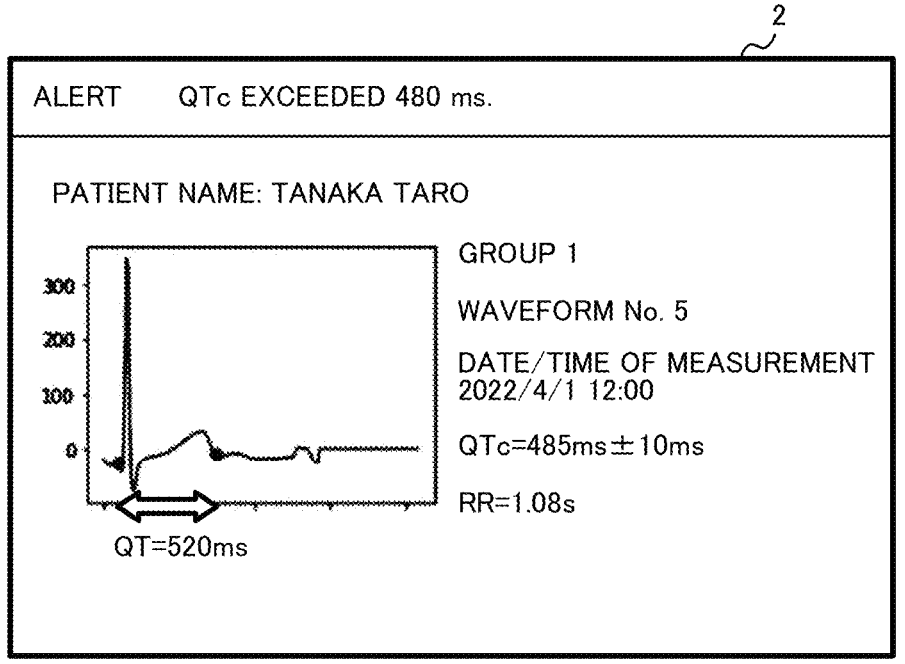
FIG. 8 is a schematic diagram for explaining a method by which an output section causes an information terminal to display information about the positions of predetermined types of wave.

FIG. 8 is a schematic diagram for explaining a method by which the output section 336 causes the information terminal 2 to display information about the positions of predetermined types of wave. On the basis of the display information received from the electrocardiogram analyzing apparatus 3, the information terminal 2 displays the information about the positions of predetermined types of wave on the display section. In the example in FIG. 8, the information terminal 2 displays, as information about the positions of predetermined types of wave, a representative waveform of a group whose statistic of QT or QTc is equal to or greater than a predetermined threshold, in association with a subject of analysis.

The information displayed by the information terminal 2 is not limited to the specific information depicted here, but, as information about the positions of predetermined types of wave, the information terminal 2 may display QT, QTc, a statistic of QT, a statistic of QTc, a timing at which $\Delta$QT, $\Delta$QTc, $\Delta$QT, or $\Delta$QTc exceeds a predetermined threshold, an assessment result as to whether or not a dose should be reduced or increased, an assessment result as to whether or not a heartbeat is anomalous, or an assessment result as to whether or not a group is anomalous which are mentioned above, or the like. Thereby, an analyst need not see the whole range of electrocardiogram data of a subject of analysis, and accordingly can analyze the electrocardiogram data efficiently.

[Flowchart of Electrocardiogram Analysis Method]

Figure 9:
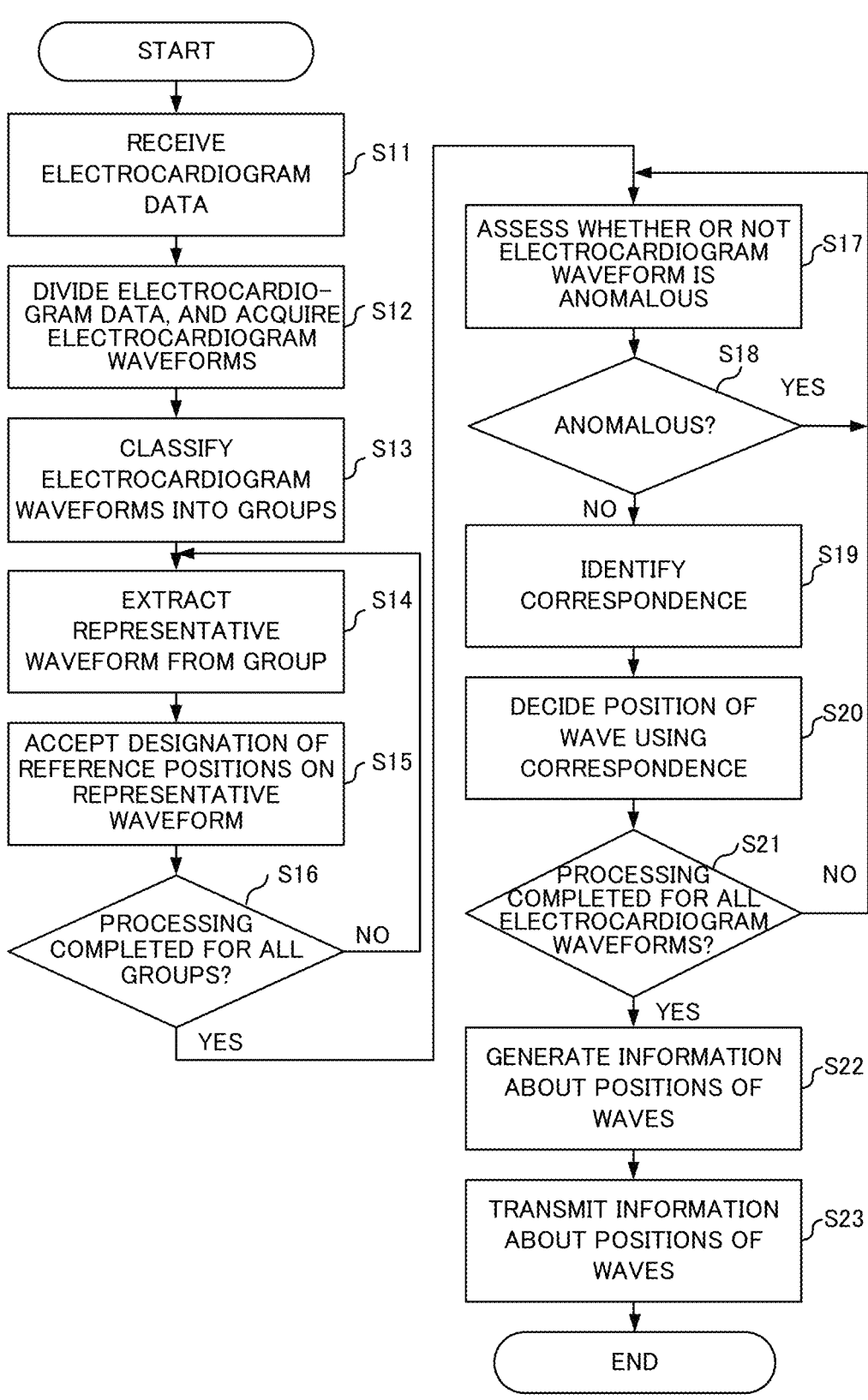
FIG. 9 is a figure depicting a flowchart of an electrocardiogram analysis method executed by an electrocardiogram analyzing apparatus according to the embodiment.

FIG. 9 is a figure depicting a flowchart of an electrocardiogram analysis method executed by the electrocardiogram analyzing apparatus 3 according to the present embodiment. In the electrocardiogram analyzing apparatus 3, the acquiring section 331 receives electrocardiogram data transmitted by the electrocardiograph 1 via the communicating section 31 (S11). The acquiring section 331 acquires a plurality of electrocardiogram waveforms generated by dividing the received electrocardiogram data into heartbeat-by-heartbeat pieces of data (S12).

The classifying section 332 classifies the plurality of electrocardiogram waveforms acquired by the acquiring section 331 into a plurality of groups on the basis of shape similarity (S13). The classifying section 332 extracts, from a group selected from the decided plurality of groups, a representative waveform corresponding to at least one electrocardiogram waveform belonging to the group (S14).

The accepting section 333 accepts designation of reference positions of predetermined types of wave on the representative waveform extracted from the selected group (S15). For example, on the basis of operation by an analyst on the information terminal 2, the accepting section 333 accepts designation of reference positions of predetermined types of wave. In a case where designation of reference positions has not been completed for all of the plurality of groups (NO at S16), the electrocardiogram analyzing apparatus 3 repeats steps S14 to S15 for another group selected from the plurality of groups. In a case where designation of reference positions has been completed for all of the plurality of groups (YES at S16), the electrocardiogram analyzing apparatus 3 proceeds to step S17.

The assessing section 334 assesses whether or not a subject-of-analysis electrocardiogram waveform selected from the plurality of electrocardiogram waveforms is anomalous (outlier) (S17). In a case where it is assessed that the subject-of-analysis electrocardiogram waveform is anomalous (YES at S18), the electrocardiogram analyzing apparatus 3 repeats step S17 for another subject-of-analysis electrocardiogram waveform selected from the plurality of electrocardiogram waveforms. In a case where it is assessed that the subject-of-analysis electrocardiogram waveform is not anomalous (NO at S18), the electrocardiogram analyzing apparatus 3 proceeds to step S19. The analyzing section 335 identifies the correspondence between a plurality of positions, along the time axis, on a representative waveform of a group to which the subject-of-analysis electrocardiogram waveform belongs, and a plurality of positions on the subject-of-analysis electrocardiogram waveform along the time axis (S19).

The analyzing section 335 decides, as the positions of predetermined types of wave included in the subject-of-analysis electrocardiogram waveform, positions on the subject-of-analysis electrocardiogram waveform corresponding to the reference positions on the representative waveform represented by the identified correspondence (S20). In a case where decision of the positions of waves has not been completed for all of the plurality of electrocardiogram waveforms (NO at S21), the electrocardiogram analyzing apparatus 3 repeats step S20 for another subject-of-analysis electrocardiogram waveform selected from the plurality of electrocardiogram waveforms. In a case where decision of the positions of waves has been completed for all of the plurality of electrocardiogram waveforms (YES at S21), the electrocardiogram analyzing apparatus 3 proceeds to step S22.

The analyzing section 335 generates information about the decided positions of the predetermined types of wave (S22). The output section 336 transmits, to the information terminal 2 via the communicating section 31, display information for displaying information about the positions of the predetermined types of wave generated by the analyzing section 335 (S23). On the basis of the display information received from the electrocardiogram analyzing apparatus 3, the information terminal 2 displays the information about the positions of the predetermined types of wave on the display section.

Effects of Embodiment

Since various types of wave such as normal T waves, flat T waves, or negative T waves have forms that are different from each other, it has conventionally been difficult for a computer to highly precisely sense the positions of the various types of wave from an electrocardiogram waveform, in some cases. To cope with this, in the electrocardiogram analysis system S according to the present embodiment, the electrocardiogram analyzing apparatus 3 classifies heartbeat-by-heartbeat electrocardiogram waveforms into a plurality of groups on the basis of shape similarity, and accepts, from an analyst, designation of the positions of predetermined types of wave on a representative waveform of each group. Then, the electrocardiogram analyzing apparatus 3 decides the positions of predetermined types of wave in a subject-of-analysis electrocardiogram waveform by identifying the correspondence between a plurality of positions on a representative waveform of each group along the time axis, and a plurality of positions on the subject-of-analysis electrocardiogram waveform along the time axis. Thereby, the electrocardiogram analysis system S can decide the positions of the predetermined type of waves taking into consideration variations of forms of waves, and can improve the precision of sensing of the positions of the predetermined types of wave in the electrocardiogram waveform.

Although the present disclosure has been explained by using an embodiment thus far, the technical scope of the present disclosure is not limited by the scope of the description of the embodiment described above. It is obvious for those skilled in the art that diverse changes or improvements can be made to the embodiment described above. It is obvious from the description of claims that embodiments realized by making such changes or improvements can also be included in the technical scope of the present disclosure.

A processor of the electrocardiogram analyzing apparatus 3 executes each step (step) included in the electrocardiogram analysis method depicted in FIG. 9. That is, the processor of the electrocardiogram analyzing apparatus 3 executes the electrocardiogram analysis method depicted in FIG. 9 by executing a program for executing the electrocardiogram analysis method depicted in FIG. 9. The steps included in the electrocardiogram analysis method depicted in FIG. 9 may be omitted partially, the order of the steps may be changed, or a plurality of steps in the steps may be performed in parallel.

What is claimed is:

1. An electrocardiogram analyzing apparatus comprising:

a memory configured to store a plurality of electrocardiogram waveforms of a subject-of-analysis for at least 24 hours, the plurality of electrocardiogram waveforms configured to be determined based on data from at least one electrocardiograph lead connectable to the subject-of-analysis;

a non-transitory computer-readable medium having stored therein a plurality of executable instructions;

a processor executing the instructions; and a communicating section configured to transmit and receive data from an electrocardiograph and an information terminal, and notify the processor of the data received from the electrocardiograph and the information terminal;

wherein the processor is configured to:

acquire the plurality of electrocardiogram waveforms generated by dividing electrocardiogram data into heartbeat-by-heartbeat pieces of data;

classify the plurality of electrocardiogram waveforms into a plurality of groups to make a distance between shapes of any two electrocardiogram waveforms in one group short;

calculate a centroid waveform which is a center of mass of the plurality of electrocardiogram waveforms belonging to a selected group which is one of the plurality of groups;

extract, from the plurality of electrocardiogram waveforms belonging to the selected group, a representative waveform a distance from the centroid waveform which satisfies a predetermined condition indicating that the representative waveform is similar to the centroid waveform;

accept a reference position of a Q wave and a reference position of a T wave on the representative waveform;

identify correspondence between a first plurality of positions, along a time axis, on the representative waveform of a group of the plurality of groups to which a subject-of-analysis electrocardiogram waveform belongs, and a second plurality of positions on the subject-of-analysis electrocardiogram waveform along a time axis, to minimize a total value of distances between the first plurality of positions and the second plurality of positions, and decide, as a position of the Q wave and a position of the T wave included in the subject-of-analysis electrocardiogram waveform, a position on the subject-of-analysis electrocardiogram waveform corresponding to the reference position of the Q wave and the reference position of the T wave on the representative waveform represented by the correspondence, the communicating section is adapted to transmit information for displaying the representative waveform to the information terminal, the communicating section is adapted to receive information indicating a position of the Q wave and a position of the T wave designated by the user on the representative waveform displayed on the information terminal through an operation section of the information terminal, and the processor is adapted to accept the positions of the Q wave and the T wave designated by the user which the information received by the communicating section indicates, as the reference position of the Q wave and the reference position of the T wave; and assess whether or not a dose of a medicine for the subject-of-analysis should be reduced or increased based on the information received by the communicating section.

2. The electrocardiogram analyzing apparatus according to claim 1, wherein the processor is configured to accept each of the reference position of the Q wave and the reference position of the T wave on the representative waveform, and the processor is configured to decide each of the position of the Q wave and the position of the T wave included in the subject-of-analysis electrocardiogram waveform.

3. The electrocardiogram analyzing apparatus according to claim 2, wherein the processor is configured to calculate an interval between the position of the Q wave and the position of the T wave, and/or a calibrated interval calculated by calibrating the interval by using a heart rate identified from the subject-of-analysis electrocardiogram waveform.

4. The electrocardiogram analyzing apparatus according to claim 3, wherein the processor is further configured to, under a condition that a statistic of intervals or calibrated intervals in the plurality of electrocardiogram waveforms belonging to the group is equal to or greater than a threshold, output an electrocardiogram waveform having a highest similarity with the representative waveform of the group in the plurality of electrocardiogram waveforms belonging to the group.

5. The electrocardiogram analyzing apparatus according to claim 3, wherein the processor is configured to:

assess that the group is anomalous in a case where a value representing variations in intervals or calibrated intervals in a plurality of electrocardiogram waveforms belonging to the group is equal to or greater than a threshold, and assess that the group is not anomalous in a case where the value representing the variations is lower than the threshold, and generate information that is different depending on whether it is assessed that the group is anomalous or it is assessed that the group is not anomalous.

6. The electrocardiogram analyzing apparatus according to claim 5, wherein the processor is configured to accept designation of each of the reference position of the Q wave and the reference position of the T wave on the representative waveform of the group assessed as being anomalous by the processor again.

7. The electrocardiogram analyzing apparatus according to claim 1, wherein the representative waveform is any one electrocardiogram waveform having a highest similarity with a waveform, which is a statistic of a plurality of electrocardiogram waveforms, belonging to the selected group in the plurality of electrocardiogram waveforms belonging to the selected group.

8. The electrocardiogram analyzing apparatus according to claim 1, wherein the processor is configured to cause the information terminal to display the representative waveform, and accept, on the information terminal and as the reference position of the Q wave and the reference position of the T wave, a position designated on the representative waveform.

9. The electrocardiogram analyzing apparatus according to claim 8, wherein the processor is configured to accept designation of positions for the representative waveform on the information terminal multiple times, and accept, as the reference position of the Q wave and the reference position of the T wave, a position corresponding to a statistic of a plurality of designated positions.

10. The electrocardiogram analyzing apparatus according to claim 1, wherein the processor is further configured to:

assess that an electrocardiogram waveform belonging to the group is not anomalous in a case where a similarity between the electrocardiogram waveform and a waveform, which is a statistic of a plurality of electrocardiogram waveforms, belonging to the group is equal to or greater than a threshold, and assess that the electrocardiogram waveform is anomalous in a case where the similarity is lower than the threshold, wherein decide the position of the predetermined type of wave under a condition that the subject-of-analysis electrocardiogram waveform is assessed as being not anomalous by the processor.

11. An electrocardiogram analysis method comprising:

transmitting and receiving data, via communication section, from an electrocardiograph and an information terminal, and notifying a control section of the data received from the electrocardiograph; and executing by a processor, of storing, in a memory, a plurality of electrocardiogram waveforms of a subject-of-analysis for at least 24 hours, the plurality of electrocardiograms waveforms configured to be determined based on data from at least one electrocardiograph lead subject-of-analysis, the plurality of electrocardiograms waveforms generated by dividing electrocardiogram data into heartbeat-by-heartbeat pieces of data;

classifying the plurality of electrocardiogram waveforms into a plurality of groups to make a distance between shapes of any two electrocardiogram waveforms in one group short;

calculating a centroid waveform which is a center of mass of the plurality of electrocardiogram waveforms belonging to a selected group which is one of the plurality of groups;

extracting, from the plurality of electrocardiogram waveforms belonging to the selected group, a representative waveform a distance from the centroid waveform which satisfies a predetermined condition indicating that the representative waveform is similar to the centroid waveform;

accepting a reference position of a Q wave and a reference position of a T wave on the representative waveform;

identifying correspondence between a first plurality of positions, along a time axis, on the representative waveform of a group of the plurality of groups to which a subject-of-analysis electrocardiogram waveform belongs, and a second plurality of positions on the subject-of-analysis electrocardiogram waveform along a time axis, to minimize a total value of distances between the first plurality of positions and the second plurality of positions, and deciding, as positions of the Q wave and the T wave included in the subject-of-analysis electrocardiogram waveform, a position on the subject-ofanalysis electrocardiogram waveform corresponding to the reference position of the Q wave and the reference position of the T wave on the representative waveform represented by the correspondence, transmitting, via the communicating section, information for displaying the representative waveform to the information terminal, receiving, via the communicating section, information indicating positions of the Q wave and the T wave designated by the user on the representative waveform displayed on the information terminal through an operation section of the information terminal, and accepting, by the processor, the positions of the Q wave and the T wave designated by the user which the information received by the communicating section indicates, as the reference position of the Q wave and the reference position of the T wave;

and assessing whether or not a dose of a medicine for the subject-of-analysis should be reduced or increased based on the information received by the communicating section.

12. The electrocardiogram analyzing apparatus according to claim 1, wherein the representative waveform is a statistic of the plurality of electrocardiogram waveforms.

13. An electrocardiogram analyzing system including:

a memory configured to store a plurality of electrocardiogram waveforms of a subject-of-analysis for at least 24 hours, the plurality of electrocardiogram waveforms configured to be determined based on data from at least one electrocardiograph lead connectable to the subject-of-analysis;

an electrocardiogram analyzing apparatus; and an information terminal, the electrocardiogram analyzing apparatus comprising:

a processor; and a communicating section configured to transmit and receive data from an electrocardiograph the information terminal, and notify the processor of the data received from the electrocardiograph the information terminal, wherein the processor is configured to:

acquire the plurality of electrocardiogram waveforms generated by dividing electrocardiogram data into heartbeat-by-heartbeat pieces of data;

classify the plurality of electrocardiogram waveforms into a plurality of groups to make a distance between shapes of any two electrocardiogram waveforms in one group short;

calculate a centroid waveform which is a center of mass of the plurality of electrocardiogram waveforms belonging to a selected group which is one of the plurality of groups;

extract, from the plurality of electrocardiogram waveforms belonging to the selected group, a representative waveform a distance from the centroid waveform which satisfies a predetermined condition indicating that the representative waveform is similar to the centroid waveform;

accept a reference position of a Q wave and a reference position of a T wave on the representative waveform;

identify correspondence between a first plurality of positions, along a time axis, on the representative waveform of a group of the plurality of groups to which a subject-of-analysis electrocardiogram waveform belongs, and a second plurality of positions on the subject-of-analysis electrocardiogram waveform along a time axis, to minimize a total value of distances between the first plurality of positions and the second plurality of positions, and decide, as positions of the Q wave and the T wave included in the subject-of-analysis electrocardiogram waveform, a position on the subject-of-analysis electrocardiogram waveform corresponding to the reference position of the Q wave and the reference position of the T wave on the representative waveform represented by the correspondence, the communicating section is adapted to transmit information for displaying the representative waveform to the information terminal, the communicating section is adapted to receive information indicating positions of the Q wave and the T wave designated by the user on the representative waveform displayed on the information terminal through an operation section of the information terminal, and the processor is adapted to accept the positions of the Q wave and the T wave designated by the user which the information received by the communicating section indicates, as the reference position of the Q wave and the reference position of the T wave, and assess whether or not a dose of a medicine for the subject-of-analysis should be reduced or increased based on the information received by the communicating section, and the information terminal comprising:

a display section that displays information about the position of the predetermined type of wave included in the subject-of-analysis electrocardiogram waveform.

14. An electrocardiogram analyzing apparatus comprising:

a memory configured to store a plurality of electrocardiogram waveforms of a subject-of-analysis for at least 24 hours, the plurality of electrocardiogram waveforms configured to be determined based on data from at least one electrocardiograph lead connectable to the subject-of-analysis;

a non-transitory computer-readable medium having stored therein a plurality of executable instructions;

a processor executing the instructions; and a communicating section configured to transmit and receive data from an electrocardiogra and an information terminal, and notify the processor of the data received from the electrocardiogra and the information terminal;

wherein the processor is adapted to execute:

acquire, the plurality of electrocardiogram waveforms generated by dividing electrocardiogram data into heartbeat-by-heartbeat pieces of data;

classify the plurality of electrocardiogram waveforms into a plurality of groups to make a distance between shapes of any two electrocardiogram waveforms in one group short;

calculates a centroid waveform which is a center of mass of the plurality of electrocardiogram waveforms belonging to a selected group which is one of the plurality of groups;

extract a representative waveform that is the most similar to the centroid waveform among the plurality of electrocardiogram waveforms belonging to the selected group;

accept a reference position of a Q wave and a reference position of a T wave on the representative waveform;

identify correspondence between a first plurality of positions, along a time axis, on the representative waveform of a group of the plurality of groups to which a subject-of-analysis electrocardiogram waveform belongs, and a second plurality of positions on the subject-of-analysis electrocardiogram waveform along a time axis, to minimize a total value of distances between the first plurality of positions and the second plurality of positions, and decide, as positions of the Q wave and the T wave included in the subject-of-analysis electrocardiogram waveform, a position on the subject-of-analysis electrocardiogram waveform corresponding to the reference position of the Q wave and the reference position of the T wave on the representative waveform represented by the correspondence, the communicating section is adapted to transmit information for displaying the representative waveform to the information terminal, the communicating section is adapted to receive information indicating positions of the Q wave and the T wave designated by the user on the representative waveform displayed on the information terminal through an operation section of the information terminal, and the processor is adapted to accept the positions of the Q wave and the T wave designated by the user which the information received by the communicating section indicates, as the reference position of the Q wave and the reference position of the T wave;

and assess whether or not a dose of a medicine for the subject-of-analysis should be reduced or increased based on the information received by the communicating section.

* * * * *